(12) United States Patent
Schaffner

(10) Patent No.: US 8,137,683 B2
(45) Date of Patent: Mar. 20, 2012

(54) PROCESS FOR THE PREPARATION OF DISPERSIONS

(75) Inventor: David Schaffner, Rheinfelden (CH)

(73) Assignee: DSM IP Assets B.V., Herleen (NL)

( * ) Notice: Subject to any disclaimer, the term of this patent is extended or adjusted under 35 U.S.C. 154(b) by 1125 days.

(21) Appl. No.: 10/481,167

(22) PCT Filed: Jun. 10, 2002

(86) PCT No.: PCT/EP02/06328
§ 371 (c)(1),
(2), (4) Date: Dec. 17, 2003

(87) PCT Pub. No.: WO02/102298
PCT Pub. Date: Dec. 27, 2002

(65) Prior Publication Data
US 2004/0209963 A1    Oct. 21, 2004

(30) Foreign Application Priority Data
Jun. 19, 2001    (EP) .................................... 01114619

(51) Int. Cl.
*A61K 9/00*    (2006.01)
*A61K 9/14*    (2006.01)
*A61K 31/015*    (2006.01)
(52) U.S. Cl. ........................... 424/400; 424/46; 514/763
(58) Field of Classification Search .................. 502/209; 424/400, 46; 514/763
See application file for complete search history.

(56) References Cited

U.S. PATENT DOCUMENTS

| 3,625,863 | A | * | 12/1971 | Heller et al. | ............... | 502/209 |
| 4,522,743 | A |   | 6/1985  | Horn et al. |   |   |
| 4,726,955 | A | * | 2/1988  | Horn et al. | ............... | 426/73 |
| 5,639,441 | A | * | 6/1997  | Sievers et al. | ............... | 424/9.3 |

FOREIGN PATENT DOCUMENTS

| DE | 29 43 267 |   | 5/1981 |
| DE | 199 04 990 |   | 4/2000 |
| EP | 0 065 193 |   | 11/1982 |
| EP | 0 239 949 |   | 10/1987 |
| EP | 0 677 332 |   | 10/1995 |
| EP | 1 097 705 |   | 5/2001 |
| WO | WO 97/31691 |   | 9/1997 |
| WO | WO 98/16204 | * | 4/1998 |
| WO | WO 99/52504 |   | 10/1999 |
| WO | WO 9952504 | * | 10/1999 |
| WO | WO 00/15329 |   | 3/2000 |

OTHER PUBLICATIONS

Berger, T., "Mit verdichteten Gasen kristallisieren", *Gas Aktuell*, vol. 52, pp. 21-25.
Derwent English abstract of DE 199 04 990, Apr. 27, 2000.
Derwent English abstract of DE 29 43 267, May 7, 1981.
Bungert, B., et al., "Innovative Verfahren mit komprimierten Gasen", *Chemie Inbenieur Technik*, vol. 69, pp. 298-311 (1997).

* cited by examiner

*Primary Examiner* — Robert A Wax
*Assistant Examiner* — Aradhana Sasan
(74) *Attorney, Agent, or Firm* — Baker Donelson, Bearman, Caldwell & Berkowitz, P.C.

(57) ABSTRACT

The present invention relates to a process of a dispersion of an active substance or composition in a aqueous phase which comprises dispersing in an aqueous phase a solution of such substance or composition in dimethylether or in a C4-hydrocarbon or mixtures thereof in super- or nearcritical state, decompressing the mixture and separating the dispersion from the gaseous solvent.

18 Claims, 2 Drawing Sheets

PROCESS FOR THE PREPARATION OF DISPERSIONS

This application is the National Stage of International Application No. PCT/EP02/06328, filed Jun. 10, 2002.

The present invention relates to a process for the preparations of aqueous dispersions. More particularly, the present invention relates to a process for the preparation of a dispersion of an active substance or composition in an aqueous phase. In accordance with the present invention, aqueous dispersions of an active substance or composition are prepared by a process which comprises dispersing in an aqueous phase a solution of such substance or composition in dimethylether or in a $C_4$-hydrocarbon or mixtures thereof in super- or nearcritical state, decompressing the mixture and separating the dispersion from gaseous solvent.

The term "dispersion" as used herein encompasses emulsions and suspensions and refers to systems wherein the dispersed particles are in the micro or nano size range and, preferably, have a mean particle diameter of about 50 to about 300 nm. The term "active substance or composition" denotes any substance or composition which is soluble in dimethylether or $C_4$-hydrocarbons and substantially water-insoluble and which may be solid or liquid under ambient conditions and which usually exerts a physiological activity. Examples of such active substances are especially the fat-soluble vitamins A, D, E, K; and the carotenoids like β-carotene, canthaxanthin, apocarotenal, astaxanthin, apoester, lutein, lycopene, zeaxanthin, citranaxanthin, torularhodin; fat-soluble pharmaceuticals; other fat-soluble (health care) ingredients like PUFA (polyunsaturated fatty acids), curcumin, coenzyme Q10, α-lipoic acid.

Examples of $C_4$-hydrocarbons are hydrocarbons having four carbon atoms which can be saturated such as n-butane and isobutane, or unsaturated such as 1-butene, trans-butene and isobutene. Of these, trans-butene, 1-butene and dimethylether, especially 1-butene, are preferred, particularly for the preparation of aqueous β-carotene dispersions.

Figure 1:
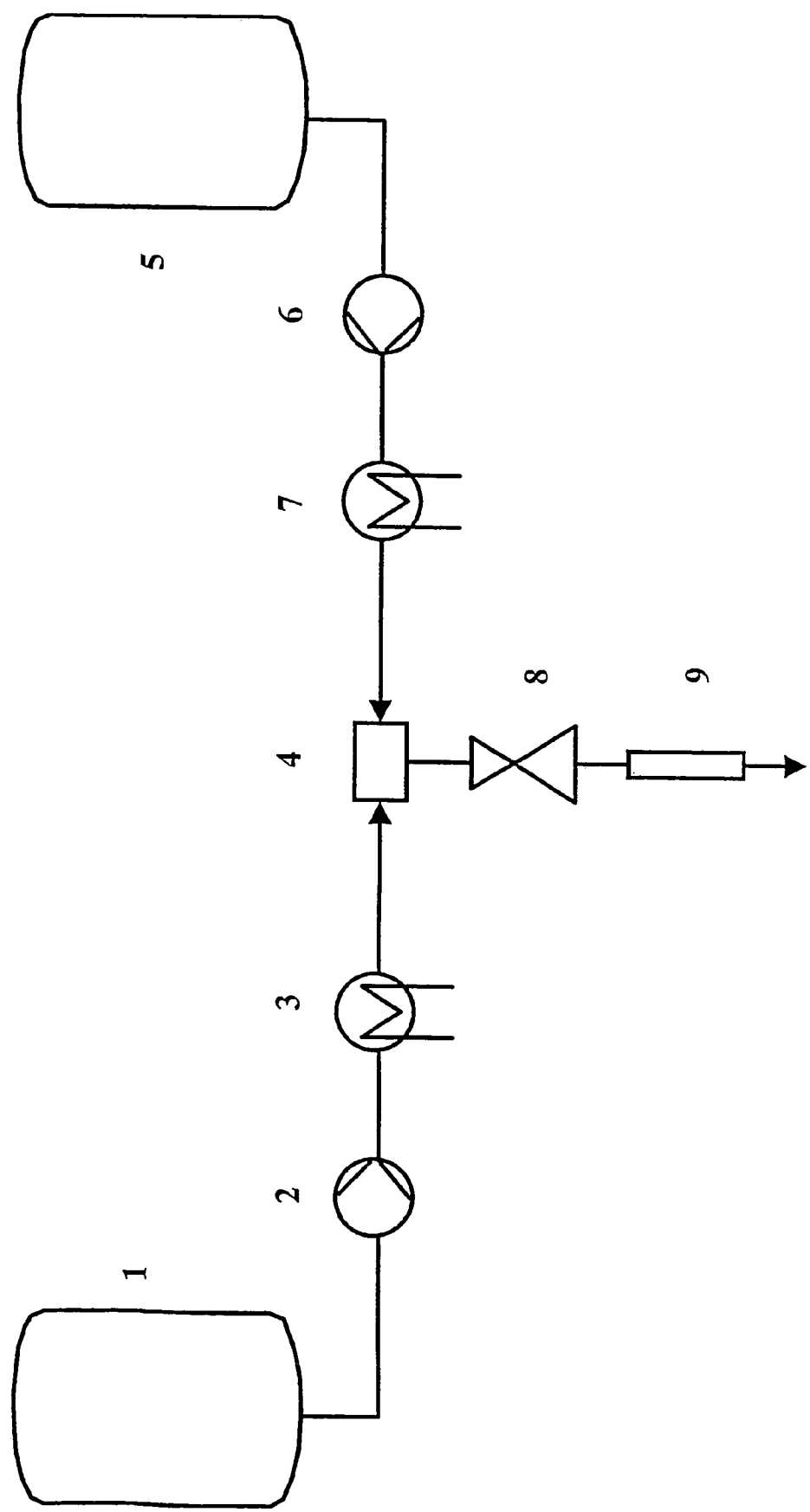

The process of the present invention is suitably carried out by individually feeding an aqueous phase and a solution of an active substance or composition in the appropriate solvent in super- or nearcritical state into a mixing chamber and decompressing the mixture. Schematically, the process of this invention can be carried out as depicted in FIG. 1. The active substance or composition is dispersed in an appropriate pressurized solvent, e.g., dimethylether, in an autoclave 1. The pressure of the solvent in autoclave 1 should be above the saturation vapor pressure. The dispersion obtained is fed by means of a high pressure pump 2 (e.g., a diaphragm pump Lewa Typ EL-3; supplier: HERBERT OTT AG, Missionsstrasse 22, CH-4003 Basel) into a mixing chamber 4 via a heat exchanger (e.g., a double-pipe heat exchanger) 3 in such a manner that temperature and pressure are close to or exceed the critical constants of the solvent, i.e., the solvent reaches the super- or nearcritical state. For instance, the pressure is about 45 bar to about 2000 bar, conveniently about 45 bar to about 300 bar, and preferably about 80 bar to about 200 bar. In a second autoclave 5 the aqueous phase which may contain additional agents such as stabilizers or surfactants is fed through a high pressure pump 6 (e.g., a piston pump LABOMATIC HD-300; supplier: LABOMATIC Instruments AG, Ringstr.13, CH-4123 Allschwil) and a heat exchanger (e.g., a double-pipe heat exchanger) 7 to the mixing chamber 4 at a pressure substantially corresponding to that build up by pumps 2 and 6 and at a temperature sufficient to maintain super- or nearcritical conditions in the mixing chamber 4. In the mixing chamber 4 the phases are mixed and decompressed through an aperture 8, then pass a residence zone 9 thus producing a finely dispersed aqueous, solvent-free suspension or emulsion.

The pumps 2 and 6 may be any pump conventionally used in high-pressure technology such as diaphragm or piston pumps. For the heat-exchangers 3 and 7 conventional heat exchangers such as tubular or double-pipe exchangers may be used. The autoclaves 1 and 5 (e.g., METIMEX Typ HPM, supplier: PREMEX REACTOR AG, Industriestrasse 11, Postfach 444) are suitably designed to permit pre-heating of their contents. The mixing chamber 4 comprises at least one inlet for the aqueous phase, at least one inlet for the non-aqueous (solvent) phase, and an outlet comprising an expansion aperture. The inlets for the aqueous phase and the solvent phase maybe arranged at an angle of between 0 degree and 180 degree, i.e., parallel or opposite to each other, or in such a manner that the two streams meet at an angle different from 0 degree and 180 degree, e.g., at an angle of about 30 to 90 degree. The mixing chamber is suitably tubular and has a dimension to secure turbulent conditions, i.e., is sufficiently small.

The aperture 8 suitably is circular and suitably has a diameter of about 0.05 mm to about 1.0 mm and preferably about 0.1 mm to 0.4 mm. By passing the aperture the dispersion will be expanded. By the expansion the compressed solvent will be evaporated and simultaneously the particle will be precipitated. After the residence time in the pipe the final dispersion can be easily separated from the gaseous solvent.

Figure 2:
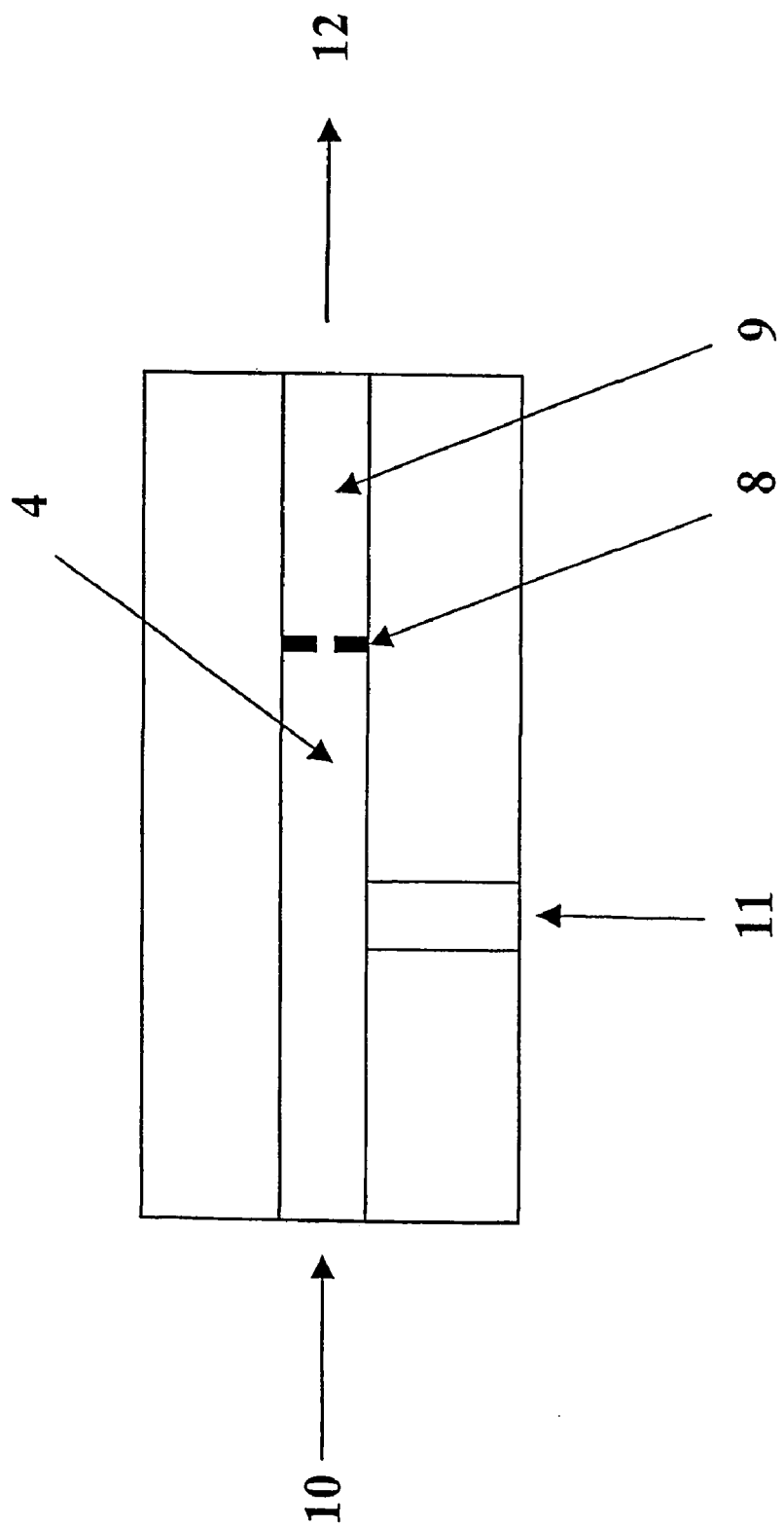

FIG. 2 shows an exemplary expansion unit consisting of mixing chamber 4 and expansion aperture 8. By mixing of the solvent phase 10 with the aqueous phase 11 in the mixing chamber a pre-emulsion (i.e., an emulsion wherein the particle size is above the ultimately desired size) results. By passing the aperture 8, the emulsion will be expanded. By the expansion the compressed solvent will be evaporated and simultaneously the particles will be precipitated. After the residence time in the residence zone 9 the final dispersion exits (12) the unit and can be easily separated from the gaseous solvent.

As will be readily understood, temperature and pressure will have to be adjusted to the particular solvent used in the process of the present invention to make sure that the system achieves the hypercritical state. Thus, when using dimethylether which has the critical constants $T_k$ 126.9° C. and $p_k$ 53.7 bar, the temperature of the fed streams to the mixing chamber will have to be at least 80° C. Preferably, when using dimethylether, the temperature is adjusted to a temperature of 80 to 160° C. The residence time of the solution of the active substance in the heat exchanger is not narrowly critical and generally is within the range of seconds. The residence time of the solution of the mixture in the mixing chamber is also not narrowly critical but is preferably no more than about 0.01 to about 0.1 seconds.

The ratio between the active substance or composition and the solvent is not narrowly critical and depends on the particular choice of the components involved. As will be readily apparent, the amount of solvent must be such to secure complete dissolution of the active substance or composition in the supercritical solvent. The ratio between the aqueous phase and the solvent phase) i.e., the ratio between the fed stream of aqueous phase and the hypercritical solvent which contains the active substance or-composition is also not narrowly critical. The upper limit of the concentration of active substance or composition in the final dispersion than can be prepared by the process of the invention ultimately depends on the solubility of the active substance or composition in the solvent. Dispersions containing up to about 50% by weight may be prepared. Suitably, the process conditions are adjusted in such a manner that the final dispersion contains about 0.1 to 20% by weight of active substance or composition, e.g., about 10% by weight.

The aqueous phase, and to some extent also the solvent phase, may contain additional ingredients, such as carriers, e.g. bovine, swine or fish gelatin, gum acacia, modified food starches, cellulose derivatives, pectins, ligninsulfonates; surfactants, e.g. sugar esters, polyglycerol fatty acid esters, Tween; stabilizers or antioxidants, e.g. sodium ascorbate, ascorbyl palmitate, dl-α-tocopherol, mixed tocopherols, BHT, BHA, or EMQ.

The dispersion or emulsion obtained can be further converted into a solid powder by means know per se, e.g. spray-drying or in a fluidized bed.

The emulsions or dispersions provided by the present invention can find use for all purposes were finely dispersed forms of substantially water-insoluble and fat-soluble substances or compositions are required, e.g., for coloring foodstuff or animal feed with carotenoids.

The invention is further illustrated by the following Examples.

EXAMPLE 1

In this Example, an installation as depicted schematically in FIG. 1 was used. A 2 liter stainless steel autoclave 5 was charged with 1100 g of water, 80 g of ascorbyl palmitate, 258 g of fish gelatin and 550 g of sugar. The aqueous phase in autoclave 5 (pre-heated to 60° C./ 6 bar $N_2$) was passed to heat exchanger 7 by piston pump 6 (LABOMATIC HD 300) at a flow rate of 90 g/min under a pressure of 150 bar where it was heated to 68.5° C. within a residence time of 6-12 sec. Autoclave 1 was charged with 50 g of β-carotene, 6 g of α-tocopherol, 22.9 g of corn oil and 740 g of dimethylether. The oily phase in autoclave 1 (pre-heated to 30° C./30 bar $N_2$) was passed to heat-exchanger 3 by diaphragm pump 2 (Lewa Typ EL 3) under a pressure of 150 bar where it was heated to 155° C. within a residence time of 5-10 sec. Aqueous phase and oily phase were simultaneously passed through mixing chamber 4 and aperture 8 having an orifice diameter of 0.25 mm to residence zone 9 where the mixture was decompressed to atmospheric pressure, producing about 5-6 kg per hour of aqueous, solvent-free dispersion of β-carotene in a gelatin/sugar matrix. The mean particle size of the dispersion was 117 nm (variance 20 nm).

EXAMPLE 2

In this Example, an installation as described in Example 1 was used. A 2 liter stainless steel autoclave 5 was charged with 1100 g of water, 80 g ascorbyl palmitate, 258 g of fish gelatin and 550 g of sugar. The aqueous phase in autoclave 5 (pre-heated to 60° C./6 bar $N_2$) was passed to heat exchanger 7 by piston pump 6 at a flow rate of 120 g/min under a pressure of 149 bar where it was heated to 64° C. within a residence time of 6-12 sec. Autoclave 1 was charged with 50 g of β-carotene, 6 g of α-tocopherol, 22.9 g of corn oil and 570 g of 1-butene. The oily phase in autoclave 1 (pre-heated to 30° C./30 bar $N_2$) was passed to heat-exchanger 3 by diaphragm pump 2 under a pressure of 149 bar where it was heated to 127° C. within a residence time of 5-10 sec. Aqueous phase and oily phase were simultaneously passed through mixing chamber 4 and aperture 8 having an orifice diameter of 0.25 mm to residence zone 9 where the mixture was decompressed to atmospheric pressure, producing about 7-8 kg per hour of aqueous, solvent-free dispersion of β-carotene in a gelatin/sugar matrix. The mean particle size of the dispersion was 223 nm (variance 87 nm).

EXAMPLE 3

In this Example, an installation as described in Example 1 was used. A 2 liter stainless steel autoclave 5 was charged with 1100 g of water, 80 g of ascorbyl palmitate, 258 g of fish gelatin and 550 g of sugar. The aqueous phase in autoclave 5 (pre-heated to 60° C./ 6 bar $N_2$) was passed to heat exchanger 7 by piston pump 6 at a flow rate of 115 g/min under a pressure of 148 bar where it was heated to 63.7° C. within a residence time of 6-12 sec. Autoclave 1 was charged with 100 g of β-carotene, 12.5 g of α-tocopherol, 45.9 g of corn oil and 590 g of trans-butene. The oily phase in autoclave 1 (pre-heated to 30° C./30 bar $N_2$) was passed to heat-exchanger 3 by diaphragm pump 2 under a pressure of 148 bar where it was heated to 137° C. within a residence time of 5-10 sec. Aqueous phase and oily phase were simultaneously passed through mixing chamber 4 and aperture 8 having an orifice diameter of 0.2 mm to residence zone 9 where the mixture was decompressed to atmospheric pressure, producing about 6-7 kg per hour of aqueous, solvent-free dispersion of β-carotene in a gelatin/sugar matrix. The produced mean particle size of the dispersion was 223 nm (variance 73 nm).

EXAMPLE 4

In this Example, an installation as described in Example 1 was used. A 2 liter stainless steel autoclave 5 was charged with 130 g of water, 62 g of ascorbyl palmitate, 242 g of fish gelatin and 384 g of sugar. The aqueous phase in autoclave 5 (pre-heated to 60° C./6 bar $N_2$) was passed to heat exchanger Z by piston pump 6 at a flow rate of 60 g/min under a pressure of 109 bar where it was heated to 75.8° C. within a residence time of 6-12 sec. Autoclave 1 was charged with 25 g of lycopene, 3.1 g of α-tocopherol, 11.5 g of corn oil and 740 g of dimethylether. The oily phase in autoclave 1 (pre-heated to 30° C./30 bar $N_2$) was passed to heat-exchanger 3 by diaphragm pump 2 under a pressure of 109 bar where it was heated to 137° C. within a residence time of 5-10 sec. Aqueous phase and oily phase were simultaneously passed through mixing chamber 4 and aperture 8 having an orifice diameter of 0.25 mm to residence zone 9 where the mixture was decompressed to atmospheric pressure, producing about 3-4 kg of aqueous, solvent-free dispersion of lycopene in a gelatin/sugar matrix per hour. The produced mean particle size of the dispersion was 171 nm (variance 60 nm).

EXAMPLE 5

In this Example, an installation as described in Example. 1 was used. A 2 liter stainless steel autoclave 5 was charged with 330 g of water, 68 g of ascorbyl palmitate, 188 g of lecithin and 1412 g of lebboline. The aqueous phase in autoclave 5 (pre-heated to 60° C./ 6 bar $N_2$) was passed to heat exchanger 7 by piston pump 6 at a flow rate of 120 g/min under a pressure of 192 bar where it was heated to 67° C. within a residence time of 6-12 sec. Autoclave 1 was charged with 50 g of β-carotene, 9.4 g of α-tocopherol, 34.4 g of corn oil and 740 g of dimethylether. The oily phase in autoclave 1 (pre-heated to 30° C./30 bar $N_2$) was passed to heat-exchanger 3 by diaphragm pump 2 under a pressure of 192 bar where it was heated to 170° C. within a residence time of 5-10 sec. Aqueous phase and oily phase were simultaneously passed through mixing chamber 4 and aperture 8 having an orifice diameter of 0.2 mm to residence zone 9 where the mixture was decompressed to atmospheric pressure, producing about 7-8 kg per hour of aqueous, solvent-free dispersion of β-carotene in a lecithin/lebboline matrix. The mean particle size of the dispersion was 174 nm (variance 36 nm).

The invention claimed is:

1. A process for the preparation of a dispersion which comprises feeding an aqueous phase and a solvent phase which comprises a solution of an active substance or composition selected from the group consisting of a fat-soluble vitamin, a pharmaceutical, a carotenoid, and a polyunsaturated fatty acid in dimethylether or in a $C_4$-hydrocarbon or mixtures thereof into a mixing chamber, wherein at least one of the solution or the aqueous phase comprises a carrier, decompressing the mixture and separating the dispersion from gaseous solvent, wherein
    (a) the active substance or composition is dispersed in dimethylether or in a $C_4$-hydrocarbon or mixtures thereof, heated in a heat exchanger for about 5 to 10 seconds, and fed into the mixing chamber by a high pressure pump in such a manner that temperature and pressure are close to or exceed the critical constants of the solvent;
    (b) the aqueous phase comprises a carrier selected from the group consisting of bovine gelatin, swine gelatin, fish gelatin, gum acacia, modified food starches, cellulose derivatives, pectins, and ligninsulfonates, and is fed into the mixing chamber at a pressure and temperature sufficient to maintain super- or nearcritical conditions;
    (c) the said two phases are mixed in the mixing chamber under turbulent conditions to produce a pre-emulsion; and
    (d) the pre-emulsion is decompressed through an aperture, which has a diameter of 0.05 mm to about 1.0 mm and then passes through a residence zone to produce the dispersion which is a finely-dispersed aqueous, solvent-free suspension or emulsion.

2. A process according to claim 1 wherein the active substance or composition is a carotenoid.

3. A process according to claim 2 wherein the carotenoid is β-carotene.

4. A process according to claim 1 wherein the solvent is selected from the group consisting of dimethylether, 1-butene, and transbutene.

5. A process according claim 1 wherein the dispersion has dispersed particles which have a mean diameter of from about 20 to about 300 nm.

6. A process according to claim 2 wherein the solvent is selected from the group consisting of dimethylether, 1-butene, and transbutene.

7. A process according to claim 3 wherein the solvent is selected from the group consisting of dimethylether, 1-butene, and transbutene.

8. A process according claim 2 wherein the dispersion has dispersed particles which have a mean diameter of from about 20 to about 300 nm.

9. A process according claim 3 wherein the dispersion has dispersed particles which have a mean diameter of from about 20 to about 300 nm.

10. A process according claim 4 wherein the dispersion has dispersed particles which have a mean diameter of from about 20 to about 300 nm.

11. A process according to claim 1 wherein the solvent phase comprises a carrier selected from the group consisting of bovine gelatin, swine gelatin, fish gelatin, gum acacia, modified food starches, cellulose derivatives, pectins, and ligninsulfonates.

12. A process according to claim 1 wherein at least one of the solution or the aqueous phase further comprises a surfactant, a stabilizer, or an antioxidant.

13. A process according to claim 1, wherein the solution of an active substance or composition in dimethylether or in a $C_4$-hydrocarbon or mixtures thereof is fed into the mixing chamber by operation of a high pressure pump and via a heat exchanger.

14. A process according to claim 1, wherein the aqueous phase is fed through a high pressure pump and a heat exchanger to the mixing chamber.

15. The process according to claim 1, wherein the two phases are in the mixing chamber for no more than about 0.01 to about 0.1 seconds.

16. The process according to claim 1, wherein the aqueous phase is heated in a heat exchanger and fed by a high pressure pump into the mixing chamber.

17. The process according to claim 1, wherein said temperature and pressure at step (a) are at least 80° C. and about 45 bar to about 2000 bar, respectively, and said pressure at step (b) is about 45 bar to about 2000 bar.

18. The process according to claim 17, wherein said pressure at step (b) substantially corresponds to said pressure at step (a).

* * * * *